United States Patent [19]

Epstein

[11] Patent Number: 4,724,212
[45] Date of Patent: Feb. 9, 1988

[54] MURINE HYBRIDOMA LYM-2 AND DIAGNOSTIC ANTIBODY PRODUCED THEREBY

[75] Inventor: Alan L. Epstein, La Canada, Calif.

[73] Assignee: Northwestern University, Evanston, Ill.

[21] Appl. No.: 738,083

[22] Filed: May 24, 1985

[51] Int. Cl.$^4$ .................. C12N 5/00; C07K 15/04
[52] U.S. Cl. .................. 435/240.27; 530/387; 435/7; 435/68; 435/172.2; 435/240.25; 935/104; 935/107; 935/110; 424/1.1; 424/85
[58] Field of Search .................. 435/240, 68, 172.27, 435/241, 948; 260/112 R, 112.5 R; 935/104, 107, 110; 424/85, 1.1; 530/387, 809

[56] References Cited

U.S. PATENT DOCUMENTS 4,513,088 4/1985 Levy et al. .................. 435/68

OTHER PUBLICATIONS

Takami, T. et al, J. Immunol. 134(2):828–834 (1985), cited in Bio. Abstract 79086651.
Marder, R. J. et al, Lab. Invest. 52(5):497–504 (1985), cited in Bio. Abstract 79086651.
Murray, L. J. et al, Clin. Exper. Immunol. 59(2):315–326 (1985), cited in Bio. Abstract 80005120.
Janossy, G. et al, Clin. Exper. Immunol. 59(2):257–266 (1985), cited in Bio. Abstract 80004036.
Jephthah, J. et al, Blood 63(2):319–325 (1984), cited in Bio. Abstract 78003585.
Winter, J. N. et al, Blood 63(1):140–146 (1984), cited in Bio. Abstract 78036670.
Delsol, G. et al, Ann. Pathol. 4(3):165–183 (1984), cited in Bio. Abstract 79031352.
Epstein, A. L. et al, J. Immunol. 133(2):1028–1036 (1984), cited in Bio. Abstract 78093014.
Gobbi, M. et al, Br. J. Haematol. 54(3):393–404 (1983), cited in Bio. Abstract 77028588.
Knowles, D. M. et al, Blood 62(1):191–199 (1983), cited in Bio. Abstract 77045013.

*Primary Examiner*—Margaret Moskowitz
*Attorney, Agent, or Firm*—Tilton, Fallon, Lungmus & Chestnut

[57] ABSTRACT

Hybridoma Lym-2 (ATCC No. HB 8613) produces murine IgG1 monoclonal antibodies specifically against normal human B cells and derived malignancies. The Lym-2 antibodies have possible clinical utility for the in vivo diagnosis of human B-cell lymphomas and leukemias.

2 Claims, No Drawings

MURINE HYBRIDOMA LYM-2 AND DIAGNOSTIC ANTIBODY PRODUCED THEREBY

This invention was made in the course of research supported in part by a grant from the National Institutes of Health (NIH R01-CA30621).

FIELD OF INVENTION

The field of the invention is hybridomas and monoclonal antibodies. More specifically, this invention relates to hybridoma-produced monoclonal antibodies which identify B-lymphocyte surface antigens, and which are useful in the diagnosis and therapy of B-cell derived human lymphomas and leukemias.

BACKGROUND AND PRIOR ART

The fusion of mouse myeloma cells and spleen cells from immunized mice by Kohler and Milstein in 1975 (Nature 256: 495-497, 1975) demonstrated for the first time that it was possible to obtain a continuous cell line making homogeneous (so-called "monoclonal") antibody. Since this seminal work, much effort has been directed to the production of various hybrid cells (called "hybridomas") and to the use of the antibody made by these hybridomas for various scientific investigations.

The analysis of lymphocyte populations in human lymphoid tissues has been greatly facilitated by the availability of monoclonal antibodies directed against lymphoid differentiation antigens. These reagents have been used to localize lymphocyte subsets topographically in the lymph node, spleen, and thymus and to phenotype lymphoid malignancies for the diagnosis and classification of the non-Hodgkin's lymphomas and leukemias.

An increasing number of monoclonal antibodies directed at B-cell surface antigens have been reported. Among the commercially available products are monoclonal antibodies to each of the heavy and light chain immunoglobulin classes. Other available reagents include BA-1 (Ambramson, C. S., Kersey, J. H., and LeBien, T. W. *J. Immunology* 125: 83-88, 1981), B1 (Nadler, L. M., Ritz, J., Hardy, K., Pesando, J. M. *J. Clin. Invest.* 67: 134-140, 1981) B2 (Nadler, L. M., Stashenko, P., Hardy, R., Van Agthoven, A., Terhorst, C., and Schlossman, S. F. *J. Immunol.* 126: 1941-1947, 1981), BL1, BL2, and BL3 (Wang, C. Y., Azzo, W., Al-Katib, A., Chiorazzi, N., and Knowles, D. M. *J. Immunol.* 133: 684-691, 1984), OKB1, OKB2, OKB4, and OKB7 (Mittler, R. S., Talle, M. A., Carpenter, K., Rao, P. E., and Goldstein, G. *J. Immunol.* 131: 1754-1761, 1983) and others. Although these monoclonal antibodies have been found to identify B-cell differentiation antigens, many cross-react with non-lymphoid tissues, have relatively low avidity of binding, or are directed against antigens which are shed into the blood. Hence, B-Cell specific monoclonal antibodies with in vivo diagnostic or therapeutic potential have not been described to date.

SUMMARY OF THE INVENTION

A hybridoma clone, designated Lym-2, was produced from the fusion of primed mouse splenocytes and mouse myeloma NS-1 cells. Hybridoma Lym-2 produced a murine IgG1 monoclonal antibody which recognizes a cell surface protein expressed in normal and malignant B lymphocytes. Immunoperoxidase staining of a panel of normal human tissues shows that Lym-2 reacts with germinal center and mantle zone B lymphocytes and interdigitating histiocytes of the lymph node. A subset of peripheral blood B cells are positive and no reactivity has been observed in human bone marrow by flow cytometric analysis. Because of the remarkable specificity of Lym-2 for human B-cells and derived malignancies, these data suggest that Lym-2 will be an appropriate reagent for in vivo diagnosis and therapy of the human B-cell lymphomas and leukemias.

DETAILED DESCRIPTION

The antigenic preparation used in obtaining the hybridoma Lym-2 consisted of the nuclei of human chronic lymphocytic leukemia (CLL) biopsy cells. See Epstein, et al. in *J. Immunol.* 133: 1028-1036, 1984 for the nuclei preparation procedure. The purified CLL nuclei were used to prepare the murine hybridoma according to well known procedures. Briefly, hybridoma clone Lym-2 was produced by the fusion of mouse myeloma NS-1 cells and BALB/c splenocytes obtained from a mouse hyperimmunized with the nuclei of CLL cells. These cell lines are generally available in the United States and other countries.

The monoclonal antibodies produced by the hybridoma Lym-2 were tested to determine the properties and specificity of Lym-2. These tests and the results are described below.

For the purpose this patent application, cultures of the hybridoma Lym-2 have been placed on deposit with the American Type Culture Collection, 12301 Parklawn Drive Rockville, Md. 20852. Hybridoma Lym-2 has been assigned the ATCC accession No. HB 8613. This deposit has been conformed to the requirements of the Budapest Treaty. The primary characteristics of hybridoma Lym-2 are as follows:

1. Origin: It was produced by fusion of NS-1 mouse myeloma cells with BALB/c mouse splenocytes primed with human CLL nuclei.
2. Cultivation: The Lym-2 hybridoma can be cultivated in RPMI-1640 medium containing 15% fetal calf serum, 100 units/ml penicillin-G, and 100 μg/ml streptomycin sulfate.
3. Properties: The Lym-2 hybridoma is not phytopathogenic and is not known to have any dangerous properties. It is tumorigenic in BALB/c mice.
4. Antibody: Lym-2 produces a murine IgG1 monoclonal antibody which specifically stains the germinal center, mantle zone, and interfollicular histiocytes of human lymph nodes and derived malignancies. It is negative on T-cells, myeloid cells, and other human tissues studied to date. Routine immunoprecipitation and immunoblot methods have failed to identify the antigen recognized by Lym-2.
5. Testing: The production of Lym-2 antibody by the hybridoma cells can be tested by indirect immunofluorescence on viable cells or 2% paraformaldehyde fixed B-cell lines, such as SU-DHL-6 or by immunoperoxidase staining on frozen sections of human lymph nodes.

The Lym-2 hybridoma may be propagated in vitro at an initial cell concentration of $2 \times 10^5$ cells/ml in RPMI-1640 medium containing 15% fetal calf serum, 100 units/ml penicillin-G, and 100 g/ml streptomycin sulfate. The cells are grown in stationary suspension culture at 37° C. in a well-humidified 5% $CO_2$ incubator and are transferred every 3-4 days.

Using the culturing procedure described above, the Lym-2 antibody may also be produced. The antibody is obtained by centrifuging the cell culture medium at 1,000 rpm for 10 minutes at 4° C. to pellet the cells. The supernatant, which contains approximately 10 g/ml of IgG1 monoclonal antibody, is then frozen at $-20°$ C. in small aliquots for use in the immunofluorescence and immunoperoxidase procedures.

To obtain larger yields of higher concentration Lym-2 antibody for the radioimmunolocalization studies, the hybridoma may be injected into BALB/c mice. The injected hybridoma will cause the formation of antibody-producing tumors after a suitable incubation time, which will result in a high concentration of the desired antibody in the bloodstream and the peritoneal exudate (ascites) of the host mouse. The Lym-2 antibody is recovered from the mice by removing the ascites fluid with a needle and syringe. The ascites is than spun at 1,000 rpm for 15 minutes at 4° C. to pellet the cells and the supernatant is filtered sequentially through a 0.8 micron and 0.22 micron filter units to remove residual debris. Using sterile technique, the filtered ascites is then stored at $-80°$ C. for long-term stability. From this preparation, approximately 2-3 mg/ml of IgG1 can be recovered and purified by standard methods. Literature references describing the foregoing procedures are: Hoogenraad, N., Helman, T., and Hoogenraad, J.: *J. Immunol. Methods*, 61: 317-320, 1983. Goding, J. W., *J. Immunol. Methods*, 39: 285-308, 1980.

EXPERIMENTAL EXAMPLES

The scientific basis of the present invention will be more fully understood from the following description of the research investigations which led to the invention.

MATERIALS AND METHODS

Antigen preparation

Nuclei from the CLL cells were prepared. Two ml of packed cells were thawed and washed once with Ca/-PIPES buffer (0.01M $CaCl_2$, $2 \times 10^{-3}$M piperazine-N,N'-bis(2-ethanesulfonic acid) in a 50-ml centrifuge tube. The sediment was then resuspended in 40 ml of Ca/PIPES buffer and thoroughly homogenized by using a motor-driven Teflon pestle to disrupt the swollen cells. The nuclei were then sedimented and resuspended in Ca/PIPES buffer containing 1% Nonidet P-40. The nuclei were then rehomogenized and checked by phase contrast microscopy to be free of contaminating cytoplasmic and membranous debris. Nuclei were then washed twice in Ca/PIPES buffer to remove the detergents, resuspended in 10 ml of PBS, and sonicated three times for 15-sec intervals to produce a more homogeneous suspension. The nuclei preparations were then frozen in 1-ml aliquots at $-85°$ C. until use.

Immunization protocol

A 1-ml aliquot of the nuclear preparation was thawed, resonicated to reduce viscosity, and emulsified in 1.5 ml of complete Freund's adjuvant (Difco Laboratories, Detroit, Mich.) by using two glass syringes and a 20-gauge microemulsifying needle (Bolab). Three 10-wk-old BALB/c female mice were injected subcutaneously at multiple sites by using a 22-gauge needle and glass syringe. Two weeks later, the mice were reinoculated as above except the nuclear extracts were prepared in incomplete adjuvant. Ten days later, the mice received a third inoculation of antigen, this time without adjuvant and by i.p. injection. Four days later, the mice were sacrificed by cervical dislocation and the spleens were removed by aseptic techiques.

Cell fusion and cloning procedures

Spleen cells were fused with 8-azaguanine-resistant mouse myeloma NS-1 cells at a ratio of 5:1, respectively, by using 40% polyethylene glycol 1540 m.w. as described by de St. Groth and Scheidegger, *J. Immunol. Methods*, 35:1, 1980. Culture supernatants from wells with active cell growth were tested by indirect immunofluorescence with fixed cell preparations as described below. Positive cultures were cloned twice on 0.5% Noble agar containing RPMI 1640 medium, 20% fetal calf serum, and antibiotics, as described by Epstein and Kaplan, *Cancer Res.*, 39: 1748, 1979.

Serologic characterization of monoclonal antibody isotypes. Hybridoma supernatants from 4-day cultures were concentrated 10 to $20\times$ in B15 minicon concentrators (Amicon, Lexington, MA) and tested in double diffusion Ouchterlony plates against rabbit anti-mouse immunoglobulin heavy chain specific antisera. The precipitin bands were read after 2 to 3 days of incubation in a well-humidified 37° C. incubator.

Live cell indirect immunofluorescence

Cells were washed twice with PBS (0.2 g $KH_2PO_4$, 0.1 g $CaCl_2.2H_2O$, 1.15 g $Na_2HPO_4$, 0.1 g $MgCl_2.6H_2O$, 0.2 g KCl, 8.0 g NaCl/liter) containing 1 mg/ml bovine serum albumin (BSA:RIA grade, Sigma Chemical, St. Louis, MO) and 0.02% sodium azide. Single cell suspensions containing $1 \times 10^6$ cells were incubated for 30 min with 100 l of monoclonal antibody supernatant at 4° C. Cells were then washed to remove excess antibody and incubated with a 1/20 dilution of fluorescein-conjugated goat anti-mouse IgG F (ab')$_2$ fragment specific (Cappel, Cochranville, PA) for 30 min at 4° C. After two additional washes, two drops of mounting solution composed of 1:1 glycerol and PBS, pH 8.0 and 2% paraformaldehyde (#4018, Polysciences, Warrington, PA) were added to each tube. The cells were mounted onto a glass slide and examined within 24 hours by epifluorescence microscopy with a Leitz Orthoplan microscope with a ploemopak 2.1 fluorescence illuminator, HBO 100 mercury lamp, and 50× water immersion objective. A minimum of 200 cells were examined for immunofluorescence staining by two independent observers. Supernatant from NS-1 myeloma cultures was used as a control to determine the background staining of each cell line.

Fixed cell indirect immunofluorescence

To examine cells for the presence of intracellular antigens, fixed cell preparations were used. Cells were washed twice with PBS containing 1 mg/ml BSA and 0.02% sodium azide and were pipetted dropwise at a concentration of $5.0 \times 10^6$ cells/ml onto Teflon-coated printed microscope slides containing 10 5-mm wells/slide. After the cells settled to the surface of the glass, the overlying fluid was quickly removed by aspiration and the cells were dried to the slide by a gentle stream of warm air. The slides were than immediately fixed in 2% paraformaldehyde in PBS for 15 min at room temperature. After fixation, the slides were rinsed in PBS and placed in acetone at −20° C. for 3 min to make the cells permeable. After a final rinse to remove the acetone, the slides were stored at 4° C. in PBS containing 0.2% sodium azide.

For the immunofluorescence assay, 35 l of hybridoma supernatant were pipetted onto each well of the printed microscope slide preparations. After 60 min of incubation at 37° C. in a humidified chamber, the slides were rinsed three times in PBS and again incubated for 30 min at 37° C. with 20 l of a 1/20 dilution of fluorescein conjugated goat anti-mouse IgG F(ab')$_2$ fragment specific. The slides were then rinsed three times in PBS, counterstained with Evans blue for 5 min at room temperature by using a freshly prepared solution containing 50 l of a 1% stock solution of Evans blue in 80 ml of PBS, rinsed a final time in PBS, and mounted with coverslips by using a 1:1 solution of glycerol and PBS, pH 8.0.

Immunoperoxidase staining

Frozen sections were prepared from human tissue biopsies obtained from the Section of Surgical Pathology, Northwestern Memorial Hospital, from specimens submitted from pathologic diagnosis. The sections were stained with the monoclonal antibody Lym-2 by using the avidin-biotin complex immunoperoxidase staining procedure as described by Hsu, et al. *J. Histochem. Cytochem.* 29: 577-580, 1981. For these experiments a ¼ dilution of Lym-2 supernatant was used. As a negative control, NS-1 supernatant which is unreactive in frozen sections, was used with each run.

Lym-2 Purification

A summary of Lym-2 purification is described as follows:
1. raise ascites in pristane primed BALB/c mice.
2. harvest ascites aseptically from peritoneal cavity.
3. remove cells by centrifugation (1,500 rpm for 20 min).
4. filter to sterilize and remove debris (0.2 micron).
5. 50% ammonium sulfate precipitation.
6. dialysis against PBS overnight at 4° C.
7. affinity purification on Protein-A sepharose. Eluate at pH 5.6-5.7.
8. dialyze against PBS overnight at 4° C.
9. ultracentrifuge at 30,000 rpm for 1 hr at 4° C.
10. membrane filter (0.2 micron).
11. store in aliquots at −80° C. until use.

RESULTS

Hybridoma clone Lym-2 was produced by the fusion of mouse myeloma NS-1 cells and BALB/c splenocytes obtained from a mouse hyperimmunized with nuclei from CLL cells. Isotypic analysis revealed that monoclonal antibody Lym-2 was of the IgG1 heavy chain subclass. The Lym-2 antibodies were identified by indirect immunofluorescence techniques with the use of paraformaldehyde-acetone-fixed cell preparations.

The reactivities of monoclonal antibodies Lym-2 on established human malignant lymphoma and leukemia cell lines are shown in Tables I and II, respectively.

TABLE I

Reactivity of Lym-2 with human malignant lymphoma cell lines by indirect immunofluorescence

| Cell Line | Lym-2[a] |
|---|---|
| Burkitt's lymphoma | |
| Raji | +[b] |
| EB3 | − |
| RAMOS | − |
| SU-AmB-1 | − |
| SU-AmB-2 | + |
| NU-AmB-1 | + |
| NK-9 | − |
| Diffuse histiocytic lymphoma | |
| SU-DHL-1 | − |
| SU-DHL-2 | − |
| SU-DHL-4 | + |
| SU-DHL-5 | − |
| SU-DHL-6 | + |
| SU-DHL-7 | − |
| SU-DHL-8 | + |
| SU-DHL-9 | + |
| NU-DHL-1 | − |
| U-937 | − |
| Undifferentiated lymphoma | |
| NU-DUL-1 | − |

[a]Fixed cell indirect immunofluorescence assay.
[b]Data expressed as (−) negative, (+) positive.

TABLE II

Reactivity of Lym-2 with human leukemia and lymphoblastoid cell lines by indirect immunofluorescence

| Cell Line | Lym-2[a] |
|---|---|
| Acute lymphoblastic leukemia | |
| T Cell | |
| Molt-4 | −[b] |
| CEM | − |
| HSB-2 | − |
| HPB-ALL | − |
| JM | − |
| Null cell | |
| REH | − |
| NALL-1 | − |
| KM-3 | − |
| B-cell | |
| BALM-2 | − |
| NALM-6 (pre-B) | − |
| NALM-1 (pre-B from CML) | − |
| Myeloid leukemia | |
| K562 (erythroid-CML) | − |
| HL-60 (promyelocytic) | − |
| ML-2 (myeloid) | − |
| TPH-1-0 (monocytic) | − |
| KG1 (myeloid) | − |
| Myeloma | |
| U-266 | − |
| ARH-77 | + |
| Lymphoblastoid | |
| BL-1 | + |
| NU-LB-1 | + |
| NU-LB-2 | − |

[a]Fixed cell indirect immunofluorescence assay.
[b]Data expressed as (−) negative; (+) positive.

In Table III, the staining reactivity of Lym-2 on human malignant lymphoma and chronic lymphocytic leukemia biopsies is shown. Indirect immunofluorescence studies showed that Lym-2 was positive on the majority of B-cell derived tumors.

TABLE III

Indirect immunofluorescence staining of human lymphoma and chronic lymphocytic leukemia biopsy cells

| Diagnosis | Lym-2 Reactivity (positive cases/total cases) |
|---|---|
| Lymphoma[a] (frozen sections of lymph node biopsies) | |

TABLE III-continued
Indirect immunofluorescence staining of human lymphoma and chronic lymphocytic leukemia biopsy cells

| Diagnosis | Lym-2 Reactivity (positive cases/ total cases) |
|---|---|
| well-differentiated lymphocytic | 3/3 |
| poorly-differentiated lymphocytic | 5/5 |
| mixed lymphocytic and histiocytic | 7/9 |
| histiocytic (B-cell type) | 12/17 |
| T-cell | 0/2 |
| Leukemia (cytospins of peripheral blood) Chronic lymphocytic | |
| B-cell type | 8/10 |
| T-cell type | 0/5 |

*a*Rappaport classification.

The immunoperoxidase staining reactivity of Lym-2 on frozen sections of normal human biopsy tissues is shown in Table IV. Lym-2 was found to be specific to B-cell lymphocytes and histiocytes in lymphoid tissues. No reactivity was demonstrated in human bone marrow or in non-lymphoid human organs.

TABLE IV
Reactivity of Lym-2 with normal human tissues

| Tissue | Lym-2 Reactivity |
|---|---|
| lymph node | + B cell zones |
| tonsil | + B cell zones |
| thymus | − |
| bone marrow* | − |
| blood* | + subset of B lymphocytes |
| adrenal | − |
| brain | − |
| breast | − |
| colon | − |
| heart | − |
| liver | − |
| lung | − |
| pancreas | − |
| salivary gland | − |
| skin | − |
| skeletal muscle | − |
| smooth muscle | − |
| thyroid | − |

*Determinations made by flow cytometric analysis on viable cells in suspension.

The immunoreactivity of Lym-2 on human solid tumor cell lines was determined by indirect immunofluorescence techniques on fixed cell preparations. As shown in Table V, Lym-2 was not found reactive on the cell with any of the 26 cell lines tested.

TABLE V
Immunoreactivity of Lym-2 with human solid tumor cell lines

| Solid Tumors | Lym-2 Reactivity |
|---|---|
| CaCL-74-36 (melanoma) | −*a* |
| BM-166 (neuroblastoma) | − |
| Y79 (retinoblastoma) | − |
| HeLa (ovarian carcinoma) | − |
| SU-CCS-1 (clear cell sarcoma) | − |
| Colo 38 (melanoma) | − |
| C-399 (colon carcinoma) | − |
| A-172 (glioblastoma) | − |
| NCI-H69 (small cell carcinoma of lung) | − |
| IMR-5 (neuroblastoma) | − |
| Hutu-80 (colon carcinoma) | − |
| HT-29 (colon carcinoma) | − |
| 734B (breast carcinoma) | − |
| SW-80 (rhabdomyosarcoma) | − |
| SW-1503 (mesothelioma) | − |
| SW-733 (papillary carcinoma of bladder) | − |
| U118-MG (glioblastoma) | − |
| SW-872 (liposarcoma) | − |
| SW-780 (transitional cell carcinoma of bladder) | − |
| SW-1045 (synovial cell carcinoma) | − |
| SW-608 (astrocytoma) | − |
| SW-1353 (chondrosarcoma) | − |
| SW-451 (squamous cell carcinoma of esophagus) | − |
| SW-156 (hypernephroma) | − |
| NU-04 (glioblastoma) | − |
| SW-579 (squamous cell carcinoma of thyroid) | − |

*a*—: negative; +: positive by indirect immunofluorescence microscopy on fixed cell preparations.

Table VI below summarizes the major characteristics of Lym-2 antibody.

TABLE VI
Characterization of Monoclonal Antibody Lym-2

| | Lym-2 |
|---|---|
| Immunogen | CLL nuclei |
| Isotype | IgG1 |
| Antigen | unknown |
| Antigen site | cell surface |
| Lymphoid Reactivity | |
| lymph node and tonsil | B-cell zones and histiocytes |
| bone marrow | none |
| blood | subset of B lymphocytes |
| thymus | none |
| Non-Lymphoid Reactivity | none |
| Tumor Specificity | B-cell lymphomas and leukemias |

I claim:
1. The hybridoma cell-line deposited under ATCC Accession No. HB 8613.
2. The monoclonal antibody produced by the hybridoma cell-line deposited under ATCC Accession No. HB 8613 and clones thereof.

* * * * *